United States Patent
Gutsche et al.

(10) Patent No.: US 7,579,493 B2
(45) Date of Patent: Aug. 25, 2009

(54) METHOD FOR PRODUCING LINEAR OR BRANCHED FATTY ACID ESTERS BY MEANS OF HETEROGENEOUSLY CATALYSED REACTIVE RECTIFICATION WITH AN UPSTREAM REACTOR

(75) Inventors: Bernhard Gutsche, Hilden (DE); Magnus Topphoff, Düsseldorf (DE); Harald Rößler, Düsseldorf (DE); Erich Reuter, Düsseldorf (DE)

(73) Assignee: Cognis IP Managment GmbH, Duesseldorf (DE)

( * ) Notice: Subject to any disclaimer, the term of this patent is extended or adjusted under 35 U.S.C. 154(b) by 328 days.

(21) Appl. No.: 10/537,973

(22) PCT Filed: Dec. 2, 2003

(86) PCT No.: PCT/EP03/13563

§ 371 (c)(1),
(2), (4) Date: Jun. 9, 2005

(87) PCT Pub. No.: WO2004/052824

PCT Pub. Date: Jun. 24, 2004

(65) Prior Publication Data

US 2006/0052619 A1  Mar. 9, 2006

(30) Foreign Application Priority Data

Dec. 10, 2002 (DE) ................. 102 57 525

(51) Int. Cl.
*C07C 51/43* (2006.01)
*C07C 69/02* (2006.01)
(52) U.S. Cl. ........................ 554/174; 554/175; 560/231
(58) Field of Classification Search ............. 554/174, 554/175; 560/231
See application file for complete search history.

(56) References Cited

U.S. PATENT DOCUMENTS

| 4,381,407 | A | 4/1983 | Bremus et al. |
| 5,008,046 | A | 4/1991 | Bremus et al. |
| 5,177,229 | A | 1/1993 | Kahsnitz et al. |
| 6,245,727 | B1 | 6/2001 | Gutsche et al. |

FOREIGN PATENT DOCUMENTS

DE  31 46 142 A1  6/1983

(Continued)

OTHER PUBLICATIONS

Aslam et al, Esterification, 12, 4 ,2000, Kirk-Othmer Encyclopedia of chemical Technology, vol. 10, p. 477.*

(Continued)

*Primary Examiner*—Taylor Victor Oh

(57) ABSTRACT

The disclosed invention relates to a countercurrent process for the continuous esterification of $C_{1-22}$ (fatty) acids with $C_{1-10}$ monoalkanols, $C_{2-5}$ di- or trialkanols or mixtures thereof in the liquid phase in the presence of heterogeneous catalysts in a preliminary reactor (1) and in a reaction column (3), characterized in that the reaction column (3) is preceded by the preliminary reactor (1) and a separation unit (2) for the purpose of reducing the viscosity of the reaction mixture and removing the water of reaction from the system via a separation unit (2) to displace the reaction equilibrium before the reaction column (3). A further aspect of the invention concerns feeding nitrogen in at the lowermost plate of the reaction column (3) in order to increase the vapor load in the lower part of the reaction column.

13 Claims, 1 Drawing Sheet

Process concept for the economic production of long-chain fatty acid esters

FOREIGN PATENT DOCUMENTS

| | | |
|---|---|---|
| DE | 25 03 195 C3 | 10/1984 |
| EP | 0 033 929 B1 | 8/1981 |
| EP | 0 141 975 B1 | 5/1985 |
| EP | 0 334 154 B1 | 9/1989 |
| EP | 0 474 996 B1 | 3/1992 |
| GB | 2 109 265 A | 6/1983 |
| SU | 671 223 A1 | 10/1992 |
| WO | WO 90/11114 A1 | 10/1990 |

OTHER PUBLICATIONS

Stage, Chemiker-Ztg./Chem. Apparatur, vol. 87, No. 18, (1963), pp. 661-666.

Fitzer, Technische Chemie, 4th Edition, (1995), pp. 184-206.

\* cited by examiner

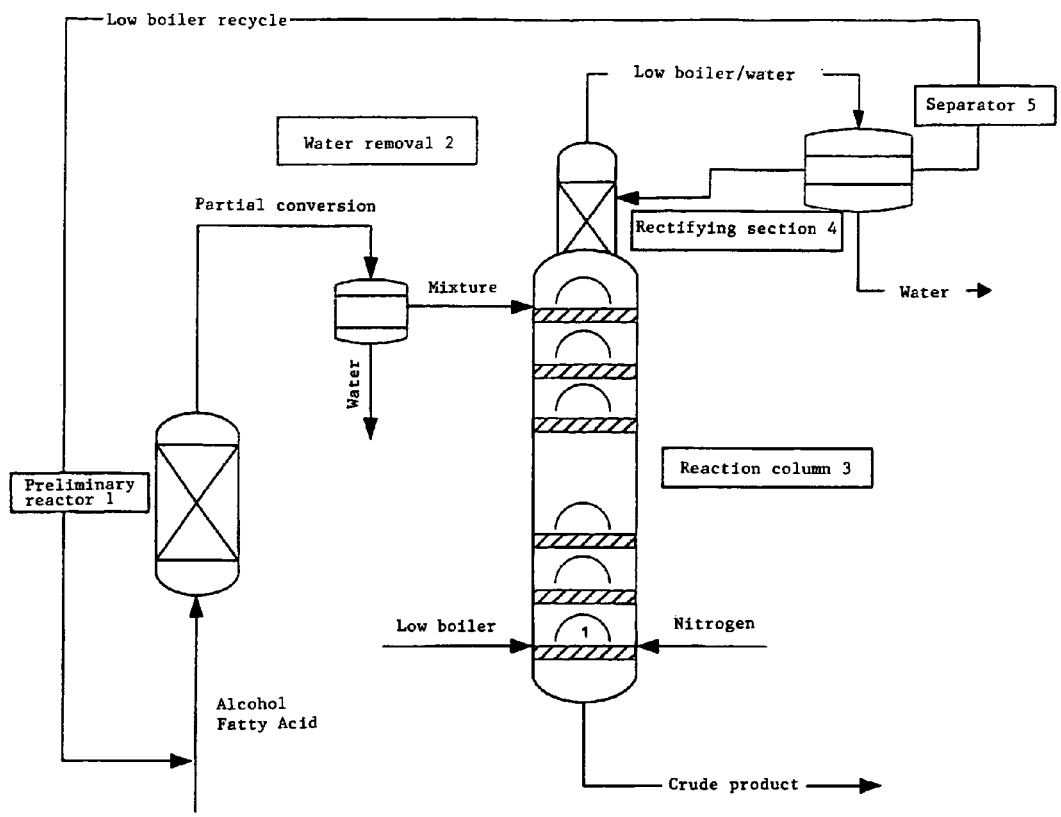
Fig. 1  Process concept for the economic production of long-chain fatty acid esters

METHOD FOR PRODUCING LINEAR OR BRANCHED FATTY ACID ESTERS BY MEANS OF HETEROGENEOUSLY CATALYSED REACTIVE RECTIFICATION WITH AN UPSTREAM REACTOR

CROSS-REFERENCE TO RELATED APPLICATIONS

This application claims priority under 35 USC § 365 from International Application PCT/EP2003/013563, filed on Dec. 2, 2003, which claims priority from German Application No. 102 57 525.8, filed on Dec. 10, 2002.

BACKGROUND OF THE INVENTION

1. Technical Field

This invention relates to a countercurrent process for the continuous esterification of $C_{1-22}$ (fatty) acids with $C_{1-10}$ monoalkanols, $C_{2-5}$ di- or trialkanols or mixtures thereof in the liquid phase in the presence of heterogeneous catalysts.

2. Background Art

Processes for the continuous esterification of fatty acids are known, cf. H. Stage, Chemiker-Ztg./Chem. Apparatur 87, No. 18, 661-666 (1963). This publication describes the esterification of fatty acids with methanol and n-butanol in multiple-section reaction columns with vapor baffle plates operated at normal pressure. However, the continuous esterification of fatty acids on an industrial scale is normally carried out in several stages in plate columns under pressures of 5 to 30 bar (cf. DE 2503195 C).

EP 0 334 154 B1 (Henkel) describes a countercurrent process for the continuous homogeneously catalyzed esterification of fatty acids with alkanols in the liquid phase in a reaction column, the catalysts and fatty acids being introduced onto the uppermost plate and the alkanols onto the lowermost plate and being reacted at a head pressure of the reaction column of 200 to 900 hPa. This process is said to avoid unwanted secondary reactions such as, for example, the dehydration of branched monoalkanols. In addition, in this homogeneously catalyzed process, the homogeneous catalyst has to be removed at the end of the reaction. This results in fairly high catalyst losses and also losses of product.

WO 90/11114 (Henkel) describes a continuous process for conducting a heterogeneously catalyzed reaction.

In discontinuous heterogeneously catalyzed processes, the solid catalyst is generally size-reduced by stirrers during its direct introduction into the reactor and has to be filtered off after the reaction. Now, WO 90/11114 describes a process in which the educts are premixed in a reactor and subsequently introduced by pumps into an external catalyst container. The reaction mixture then flows through a thin-layer or falling-film evaporator. The progress of the reaction is determined by continuous monitoring, for example of the acid value. A disadvantage of this process is that it is a discontinuous process. According to E. Fitzer, Technische Chemie, 4th Edition (1995), disadvantages of discontinuous processes are the dead times occurring during filling, emptying, heating and cooling, relatively high energy costs and relatively high labor costs.

EP 0 474 996 A1 (Hüls) describes a process for the production of esters from alcohols and acids by liquid-phase equilibrium reactions on ion exchangers. The reaction is carried out in a preliminary reactor and a rectification column with additional external reactors. On account of the severe thermal stressing of the ion exchanger in a reaction-type distillation column and the difficulties involved in separation by distillation in the presence of ion exchangers, the esterification and rectification have to be carried out in separate spaces. However, these disadvantages are reliably overcome by the process according to the invention.

The problem addressed by the present invention was to provide an economic process for the esterification of (fatty) acids with alkanols which would be a continuous, heterogeneously catalyzed process free from the disadvantages mentioned above. In addition, the color and odor of the products would be improved by less exposure to heat during production.

BRIEF SUMMARY OF THE INVENTION

This invention provides a countercurrent process for the continuous esterification of $C_{1-22}$ (fatty) acids with $C_{1-10}$ monoalkanols, $C_{2-5}$ di- or trialkanols or mixtures thereof in the liquid phase in the presence of heterogeneous catalysts in a preliminary reactor (1) and in a reaction column (3), characterized in that the reaction column (3) is preceded by the preliminary reactor (1) and a separation unit (2) for the purpose of reducing the viscosity of the reaction mixture and removing the water of reaction from the system via a separation unit (2) to displace the reaction equilibrium before the reaction column (3).

More particularly, the problem addressed by the invention was to provide an improved process for the esterification of alcohols and acids in the presence of ion exchangers with little resistance to heat where there would be no need to separate the ion exchanger from the rectification column. In the process according to the invention, the catalyst is present both in the preliminary reactor and in the rectification column. Spatial separation is not necessary. The problems stated above have been solved by the process according to the invention.

BRIEF DESCRIPTION OF THE SEVERAL VIEWS OF THE DRAWING

The process according to the invention is described with reference to the accompanying drawing (FIG. 1) which illustrates a preferred installation. However, this is not intended to limit the invention in any way.

Shown in FIG. 1 are the preliminary reactor (1), the water separator (separation unit) (2), the reaction column (3) with a plurality of bubble plates surmounted by a rectifying section (4), and a further separator (5). Also shown in FIG. 1 are the input and output flows to these installation parts. Both the preliminary reactor (1) and the rectification column (3) are filled with catalyst.

DETAILED DESCRIPTION OF THE INVENTION

In the process according to the invention, the reaction mixture of (fatty) acids and alkanols is passed through a fixed-bed reactor (preliminary reactor).

A partial reaction to the corresponding esters takes place therein. After removal of the water formed during the reaction, for example by a separation unit, this already partly reacted, far less viscous reaction mixture is introduced into the reaction column charged with catalyst. Accordingly, the viscosity of the educt stream can be clearly reduced by the use of a preliminary reactor, so that uniform flow through the fixed bed in the column is achieved. The early removal of the water of reaction before the further esterification reaction in the reaction column displaces the reaction equilibrium in favor of the ester formed.

Improved product properties and increased yields are obtained. Thus, conversions of up to 99.9%, based on the relatively low-volatility component used, can be achieved in the described process. In addition, secondary reactions are suppressed by the process according to the invention. In addition to the advantage of simple regeneration of the catalyst in the preliminary reactor, the preliminary reactor also acts as a scavenger by trapping potential catalyst poisons, so that the useful life of the catalyst in the reaction column is considerably lengthened and production costs are reduced.

The present invention relates to a countercurrent process for the continuous esterification of $C_{1-22}$ (fatty) acids with $C_{1-10}$ monoalkanols, $C_{2-5}$ di- or trialkanols or mixtures thereof in the liquid phase in the presence of heterogeneous catalysts in a preliminary reactor (1) and in a reaction column (3), characterized in that the reaction column (3) is preceded by the preliminary reactor (1) and a separation unit (2) for the purpose of reducing the viscosity of the reaction mixture and the water of reaction is removed from the system via a separation unit (2) to displace the reaction equilibrium before the reaction column (3).

The process according to the invention is described in more detail in the following with reference to the accompanying drawing (FIG. 1) which illustrates a preferred installation. However, this is not intended to limit the invention in any way.

The central element of such an installation are the preliminary reactor (1), the water separator (separation unit) (2) and the reaction column (3) with a plurality of bubble plates surmounted by a rectifying section (4). Both the preliminary reactor and the rectification column are filled with catalyst. Acids and alkanols are passed through the catalyst-filled preliminary reactor. A partial reaction to the ester takes place therein. The pre-esterified product becomes liquid and is already reduced in viscosity and is passed through a separation unit (2) located between the preliminary reactor and the reaction column. The water of reaction formed is removed from the partly reacted reaction mixture. The equilibrium of the esterification reaction is thus displaced towards the product which leads to an increased yield of esters.

Depending on the alkanol used, the water of reaction is removed by flash processes or separators, preferably with a falling-film evaporator or with a phase separator. The water is differently removed according to the alcohol used. Thus, where the short-chain alcohols methanol or ethanol are used, the water is removed from the process stream together with part of the alcohol by means of a flash tank. Where short-chain carboxylic acids are used (for example acetic acid in the production of triacetin), the water formed is removed from the stream together with part of the acetic acid in the same way. Where other alcohols, such as butanol or 2-ethylhexanol, are used, a phase separator may be used to remove the water. In addition, suitable membrane processes may be used to remove the water.

The partly reacted reaction mixture is then introduced into the reaction column (3). The heterogeneous catalyst is directly applied to the column plates. The column (3) is operated on the countercurrent principle. In general, the lower-boiling components, for example alkanols, are introduced at the bottom of the column while the higher-boiling components, such as the partly reacted reaction product, are introduced at the uppermost plate of the reactive rectification column (3). However, in the esterification of glycerol with acetic acid, the acid is introduced at the bottom of the column as the lower-boiling component.

The further esterification reaction takes place in the column. The reaction product is removed at the bottom of the column. The crude product is further worked up by distillation and optionally by deodorization. The components removed by distillation may be returned to the process by introduction into the preliminary reactor (1) and/or by introduction at the bottom of the column (3).

In the rectifying section (4) surmounting the reaction column, a mixture of low boilers (alkanol or acid) and water is distilled off. The further working up of the mixture in the separation unit (5) differs according to the low boiler used. Thus, where the short-chain alcohols methanol or ethanol are used, water is removed with the aid of an additional column. Where other alcohols, such a butanol or 2-ethylhexanol, are used, a phase separator may be used to remove the water. As another option, membrane processes may also be used, for example, to overcome azeotropic points in the system.

The low boiler removed is partly recycled to the column (3) or delivered as feed to the preliminary reactor (1). The process according to the invention is further distinguished by the fact that nitrogen is used as an additional stripping agent (entraining agent) for removing the water of reaction. The nitrogen is introduced into the column at the lowermost plate. In addition, the use of nitrogen increases the vapor load in the lower part of the column which prevents the liquid phase from "raining through". A more favorable (fatty) acid to alcohol ratio is also achieved through the use of nitrogen. For a fixed, necessary vapor load in the column, a smaller quantity of alcohol than in the conventional method of operation can be used through the use of nitrogen. This leads to economically more favorable production. At the same time, the introduction of nitrogen through the reaction column deodorizes the reaction mixture. Products with a satisfactory odor, even without additional deodorization, may be obtained in this way. This is particularly advantageous for the use of these products in cosmetics.

Accordingly, a preferred embodiment of the process according to the invention is characterized in that nitrogen is fed in at the lowermost plate of the reaction column (3) in order to increase the vapor load in the lower part of the reaction column. A particularly preferred embodiment of the process according to the invention is characterized in that nitrogen is fed in as stripping agent at the lowermost plate of the reaction column (3) for additionally removing the water of reaction. Another preferred embodiment of the process is characterized in that nitrogen is fed in at the lowermost plate of the reaction column (3) for deodorization.

Preliminary Reactor

In a preferred embodiment, the preliminary reactor (1) is a fixed-bed reactor. The catalyst material is retained in the fixed-bed reactor by suitable elements, for example by wedge-wire screens.

Reaction Column and Rectifying Section

In general, reaction columns (3) suitable for the process are any typical plate columns, such as sieve-plate columns, but especially bubble-plate columns with high liquid levels.

Typical representatives of these columns are described in EP-B 0 033 929 and in DE-A-3146142. The use of this generation of columns is of advantage because a lower excess of alcohol than in conventional columns is sufficient for achieving a complete conversion. The catalyst is directly applied to the column plates in the reaction column (3).

Temperature and Pressure

The reaction in the fixed-bed reactor takes place at temperatures of 50 to 150° C. and preferably in the range from 80 to 120° C. and under pressures of 1 to 10 bar and preferably 1 to 5 bar. The esterification in the reactive rectification column takes place at temperatures of 50 to 200° C. and preferably in the range from 80 to 150° C. and under pressures of 0.1 to 10 bar and preferably 0.1 to 5 bar.

Accordingly, a preferred embodiment of the process according to the invention is characterized in that the esterification is carried out at temperatures in the range from 50 to 200° C. and preferably at temperatures in the range from 80 to 150° C.

Alkanols

Suitable alkanols are linear or branched monoalkanols, di- or trialkanols or mixtures thereof. A preferred embodiment is characterized by the use of linear or branched $C_{1-10}$, preferably $C_{1-8}$ monoalcohols. Such monoalcohols are, for example, methanol, ethanol, propanol, butanol, pentanol and hexanol and isomers thereof. In a particularly preferred embodiment, the (fatty) acids are esterified with isopropanol or 2-ethylhexanol.

Suitable linear or branched $C_{2-5}$ di- or trialkanols are, for example, glycerol, ethanediol, propane-1,2-diol, propane-1,3-diol, butanediol and pentanediol, isomers and semiesters thereof. Accordingly, in one advantageous embodiment, the (fatty) acids are esterified with $C_{2-5}$ di- or trialkanols, preferably with $C_{2-3}$ di- or trialkanols, more particularly with glycerol.

(Fatty) Acids

Suitable starting materials for the production of the esters are (fatty) acids with a total of 1 to 22 carbon atoms. In the context of the invention, (fatty) acids are understood to be both mono- and polybasic carboxylic acids and aliphatic fatty acids.

Suitable carboxylic acids are formic acid, acetic acid and adipic acid, dodecanedioc acid, citric acid, isophthalic acid.

Aliphatic fatty acids are understood to be aliphatic carboxylic acids corresponding to the following formula:

$$R^1CO\text{—}OH \qquad (I)$$

in which $R^1CO$ is an aliphatic, linear or branched acyl group containing 6 to 22 carbon atoms and 0 and/or 1, 2 or 3 double bonds. Typical examples are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxo synthesis or in the dimerization of unsaturated fatty acids.

Technical $C_{12-18}$ fatty acids such as, for example, coconut oil, palm oil, palm kernel oil or tallow fatty acid are preferred. Head fractionated fatty acids containing 6 to 12 carbon atoms, which are obtained in large quantities in the working up of fatty acid mixtures of natural origin, are also preferably used.

A preferred embodiment is characterized by the use of $C_{6-22}$ (fatty) acids, preferably $C_{8-18}$ (fatty) acids and more particularly $C_{10-16}$ (fatty) acids.

Another advantageous embodiment of the process according to the invention is characterized in that $C_{1-5}$ carboxylic acids are esterified with $C_{2-3}$ di- or trialkanols; more particularly acetic acid is esterified with glycerol.

Catalyst

The catalysts used in the process according to the invention are selected from the group consisting of organic or inorganic, basic or acidic anion or cation exchangers or acidic clays, zeolites or specially worked up bleaching earths and catalysts based on transition metals. The use of highly acidic cation exchangers, catalysts based on transition metal oxides or organofunctional polysiloxanes is particularly preferred.

In one particular embodiment, acidic cation exchangers are preferably used as the catalyst. One example of such a catalyst is Amberlyst 17 (XE-386), a product of Rohm & Haas.

The higher-boiling component (for example (fatty) acids) and the lower-boiling component (for example monoalkanols) are preferably used in a molar ratio—calculated for the reaction of a carboxyl group with a hydroxyl group—of at most 1:2, preferably 1:1.5 and more particularly 1:1, i.e. the lower-boiling component should be present in an at most twofold excess.

Where polybasic (fatty) acids or di- or trialkanols are used, the molar ratio has to be multiplied and adapted accordingly taking the desired products (partial and/or full esters) into consideration. Again, the lower-boiling component should be present in an at most twofold excess.

It is pointed out by way of example that, for the reaction of glycerol (higher-boiling component) with acetic acid (lower-boiling component), the two components are used in a ratio of at most 1:6 (i.e. twofold excess of the acetic acid), preferably 1:4.5 and more particularly 1:3.

EXAMPLES

Example 1

Amberlyst 17 (XE-386), a product of Rohm & Haas, was used as the catalyst for the reaction. The catalyst was accommodated in a heated glass double jacket (Vmax=200 ml, D=20 mm) as a fixed-bed reactor and in the reaction column (27 bubble plates, D=50 mm, 1 bubble cap per plate). The following esterification of acetic acid with glycerol was carried out at 85° C. The glycerol was fed into the preliminary reactor together with part of the acetic acid (AA/Gly=4:1 [mol:mol]). The volumetric flow rate was 169 g/h. After the first reaction stage, the conversion amounted to 56%. The pre-esterified product was fed in as a liquid at the uppermost plate of the reaction column. The acetic acid was superheated in countercurrent and used in vapor form with a volumetric flow rate of 268 g/h. Acetic acid/water was removed at the head of the column and the reaction product at the bottom of the column. The head pressure in the column was 200 mbar. The conversion, based on glycerol, amounted to 88.7% at the bottom of the column. In order to achieve the desired conversion of >98%, the components were passed through the column a second time, an almost complete conversion (99.9%), based on glycerol, being obtained. The operating conditions were similar to those for the first passage. The composition of the product samples after the first and second passages is shown in Table 1. For working up, the reaction product was after-reacted with acetic anhydride, acetic acid was removed and triacetin was distilled.

TABLE 1

| | | Composition of the product samples Percentages by weight [% by wt.] | | | | |
|---|---|---|---|---|---|---|
| Passage | Acetic acid | Glycerol | Water | Monoacetin | Diacetin | Triacetin |
| 1 | 52.0 | 0.1 | 0.6 | 0.3 | 13.7 | 33.4 |
| 2 | 50.6 | — | <0.1 | — | 0.7 | 48.7 |

Example 2

The procedure described in Example 1 was repeated using Amberlyst 17 (XE-386), a product of Rohm & Haas, as catalyst for the reaction. The following esterification of acetic acid with glycerol was carried out at 85° C. The glycerol was fed into the preliminary reactor together with part of the acetic acid (AA/Gly=1:1 [mol:mol]). The volumetric flow rate was 174 g/h. After the first reaction stage, the conversion amounted to 23.5%. The pre-esterified product was fed in as a liquid at the uppermost plate of the reaction column. The acetic acid was used as vapor (countercurrent) with a volumetric flow rate of 262 g/h. Acetic acid/water was removed at the head of the column and the reaction product at the bottom of the column. The conversion, based on glycerol, amounted to 65% at the bottom of the column. For working up, the reaction product was after-reacted with acetic anhydride, acetic acid was removed and triacetin was distilled.

What is claimed is:

1. A countercurrent process for the continuous esterification of $C_{1-22}$ fatty acids with $C_{1-10}$ monoalkanols, $C_{2-5}$ di- or trialkanols or mixtures thereof, said process comprising:
   (a) partially reacting the fatty acids and alkanols in a preliminary reactor in the liquid phase in the presence of a heterogeneous catalyst selected from the group consisting of organic or inorganic, basic or acidic, anion or cation exchangers, acid clays and zeolites,
   (b) passing the partially-reacted reaction mixture to a separation unit,
   (c) removing water from the partially-reacted reaction mixture in the separation unit,
   (d) passing the resulting de-watered, partially-reacted reaction mixture to a countercurrent reaction column with attached rectifying column on top,
   (e) further reacting the fatty acids and alkanols in the countercurrent reaction column in the liquid phase in the presence of heterogeneous catalysts,
   (f) removing the water and excess volatile components through said rectifying column, and
   (g) removing the crude product from the bottom of said reaction column.

2. The process according to claim 1, further comprising increasing the vapour load in the lower part of the reaction column by feeding nitrogen into the reaction column at the lowermost plate.

3. The process according to claim 1, wherein the preliminary reactor is a fixed-bed reactor.

4. The process according to claim 1, wherein the esterification reaction is carried out at temperatures of 50 to 200° C.

5. The process according to claim 4, wherein the esterification reaction is carried out at temperatures of 80 to 150° C.

6. The process according to claim 1, wherein the fatty acids are esterified with $C_{1-10}$ monoalkanols.

7. The process according to claim 6, wherein the fatty acids are esterified with $C_{1-8}$ monoalkanols.

8. The process according to claim 6, wherein the fatty acids are esterified with isopropanol or 2-ethylhexanol.

9. The process according to claim 1, wherein the fatty acids are esterified with $C_{2-5}$ di- or trialkanols.

10. The process according to claim 9, wherein the fatty acids are esterified with $C_{2-3}$ di- or trialkanols.

11. The process according to claim 9, wherein the fatty acids are esterified with glycerol.

12. The process according to claim 1, wherein acidic cation exchangers are used as the catalyst.

13. The process according to claim 1, wherein the heterogeneous catalyst is selected from specially worked-up bleaching earths and catalysts based on transition metals.

* * * * *